US00PP11265P

United States Patent [19]

Zary

[11] Patent Number: Plant 11,265

[45] Date of Patent: Mar. 7, 2000

[54] HYBRID TEA ROSE PLANT NAMED 'JACOLBER'

[75] Inventor: Keith W. Zary, Thousand Oaks, Calif.

[73] Assignee: Bear Creek Gardens, Inc., Medford, Oreg.

[21] Appl. No.: 09/002,211

[22] Filed: Dec. 31, 1997

[51] Int. Cl.[7] ..... A01H 5/00

[52] U.S. Cl. ..... Plt./139

[58] Field of Search ..... Plt./139, 140

[56] References Cited

U.S. PATENT DOCUMENTS

| | | | |
|---|---|---|---|
| P.P. 6,083 | 1/1988 | Warriner | Plt./139 |
| P.P. 7,473 | 3/1991 | Warriner | Plt./139 |
| P.P. 8,507 | 12/1993 | Meilland | Plt./139 |

*Primary Examiner*—Howard J. Locker
*Attorney, Agent, or Firm*—Klarquist Sparkman Campbell Leigh & Whinston, LLP

[57] ABSTRACT

Hybrid tea rose plant has long stems ideal for cutting; dark green, glossy foliage; bright red flowers of good hybrid tea flower form; and resistance to rust and powdery mildew.

1 Drawing Sheet

The present invention relates to a new and distinct variety of rose plant of the hybrid tea class which was originated by me by crossing the variety 'MACauck' (U.S. Plant Pat. No. 5,519), with the variety 'POULman,' (U.S. Plant Pat. No. 6,264).

The primary objective of this breeding was to produce a new rose variety having the long stems, bright red flowers, and excellent hybrid tea bud form of the female parent combined with the dark green foliage and resistance to fungal diseases of the male parent. The objective was substantially achieved, along with other desirable improvements, as evidenced by the following unique combination of characteristics that are outstanding in the new variety and that distinguish it from its parents, as well as from all other varieties of which I am aware:

1. Long stems ideal for cutting;
2. Very bright red flowers;
3. Good hybrid tea bud form;
4. Dark green, glossy foliage;
5. Resistance to rust and powdery mildew infection;

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—MACauck (U.S. Plant Pat. No. 5,519).

*Pollen parent.*—POULman (U.S. Plant Pat. No. 6,264).

Classification:

*Botanical.*—Rosa hybrida.

*Commercial.*—Hybrid Tea.

FLOWER

Observations made from specimens grown in a garden environment at Somis, Calif. from January, 1996–August, 1997.

Blooming habit: Recurrent

Bud:

*Size.*—Two inches long when the petals start to unfurl.

*Form.*—The bud form is long, pointed ovoid.

*Color.*—When sepals first divide, bud color is Red Group 46A. When half blown, the upper sides of the petals are Red Group 45A; and the lower sides of the petals are Red Group 53C.

*Sepals.*—Color: Green group 138B. Surface texture: Covered with fine hairs. There are three heavily appendaged sepals. There are two unappendaged sepals with hairy edges.

*Receptacle.*—Color: Green Group 141C. Shape: Funnel. Size: Large (⅜" long×5/16" wide). Surface: Smooth.

*Peduncle.*—Length: Long (4" to 4½"). Surface: Smooth with a few small prickles. Color: Medium green and bronzy. Strength: Stiff, erect.

Bloom:

*Size.*—Large. Average open size is 5 to 5½ inches.

*Borne.*—Singly.

*Stems.*—Long (18–22").

*Form.*—When first open: High centered. Permanence: Flattens; all petals curl.

*Petalage.*—Number of petals under normal conditions: 30–35.

*Color.*—The upper sides of the petals are Red Group 45A. The reverse sides of the petals are Red Group 53C. The base of the petals has a small (⅛"×⅛"), light yellow half moon at the point of attachment. The major color on the upper side is Red Group 45A.

*Variegations.*—There are occasional white streaks on the guard petals.

*Discoloration.*—At the end of the first day: No change. By day six, on the plant, there is change in flower color from Red Group 45A to Red Group 53C (flower "blues"). By day seven or eight, the petals drop.

*Fragrance.*—Slight.

Petals:

*Texture.*—Thick.

*Shape.*—Round to slightly deltoid.

*Form.*—Tips slightly recurved, edges of outermost petals slightly quilled.

*Arrangement.*—Imbricated. Petaloids in the center are few.

*Persistence.*—Drop off cleanly.

*Lastingness.*—On the plant: Long (six to seven days). As a cut flower: Long (eight to nine days).

Reproductive parts:

*Anthers.*—Size: Large. Quantity: Many. Color: Yellow. Arrangement: Regular around styles.

*Filaments.*—Color: Reddish-brown.

*Pollen.*—Color: Gold yellow.

*Styles.*—Color: Reddish.

*Stigmas.*—Color: Greenish-white.

Plant:

*Form.*—Bush.

*Growth.*—Very vigorous; upright; branching; Height in one growing season in Somis, Calif., six feet, width four feet.

Foliage:

*Number of leaflets on normal mid-stem leaves.*—Five.

*Size.*—Very large (7"×5½").

*Quantity.*—Normal.

*Color.*—New foliage: Upper and lower surfaces; Greyed Red Group 181A. Old foliage: Upper Surface: Green Group 139A. Lower Surface: Green Group 139C.

*Shape.*—Pointed oval.

*Texture.*—Upper side: Leathery.

*Edge.*—Serrated.

*Serration.*—Single, small.

*Petiole rachis.*—Color: Green.

*Petiole underside.*—Smooth with occasional small prickles.

*Stipules.*—Medium (¾"); serrated, bearded.

*Disease resistance.*—Resistant to mildew and rust under normal growing conditions at Somis, Calif.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—Medium (⅜"); hooked downward.

*Color when young.*—Red.

Small prickles:

*Quantity.*—On main stalks: None. On laterals: None.

I claim:

1. A new and distinct variety of rose plant of the hybrid tea class, substantially as herein shown and described, characterized particularly as to novelty by long stems ideal for cutting; dark green, glossy foliage; bright red flowers; good hybrid tea form; and resistance to rust and powdery mildew.

* * * * *

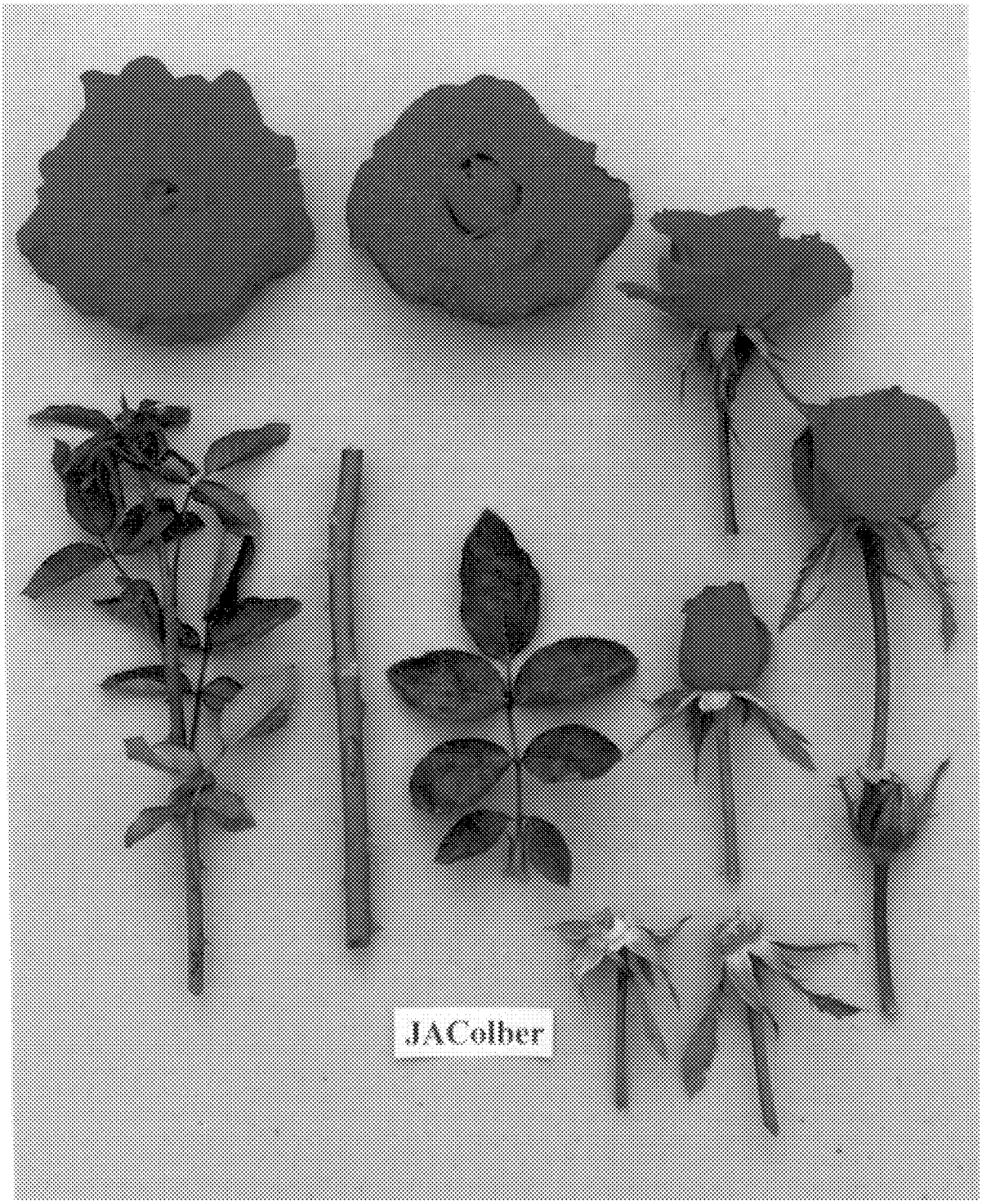
JAColber